(12) United States Patent  
Huang

(10) Patent No.: US 8,767,514 B2
(45) Date of Patent: Jul. 1, 2014

(54) TELEMETRIC SENSING USING MICROMACHINED ULTRASONIC TRANSDUCER

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 1132 days.

(21) Appl. No.: 12/326,769

(22) Filed: Dec. 2, 2008

(65) Prior Publication Data

US 2009/0141592 A1     Jun. 4, 2009

Related U.S. Application Data

(60) Provisional application No. 60/992,020, filed on Dec. 3, 2007.

(51) Int. Cl.
*H04R 23/00* (2006.01)
*A61B 8/00* (2006.01)

(52) U.S. Cl.
CPC .............. *A61B 8/4472* (2013.01); *H04R 23/00* (2013.01)
USPC .......................................... 367/181; 600/459

(58) Field of Classification Search
USPC .......................................... 367/181; 600/459
See application file for complete search history.

(56) References Cited

U.S. PATENT DOCUMENTS

| | | | |
|---|---|---|---|
| 4,413,520 A | 11/1983 | Murakami et al. | |
| 4,603,589 A | 8/1986 | Machida | |
| 5,870,351 A | 2/1999 | Ladabaum et al. | |
| 5,872,536 A * | 2/1999 | Lyons et al. | 342/70 |
| 5,906,580 A | 5/1999 | Kline-Schoder et al. | |
| 5,957,851 A | 9/1999 | Hossack | |
| 6,493,288 B2 * | 12/2002 | Khuri-Yakub et al. | 367/181 |
| 6,558,330 B1 | 5/2003 | Ayter et al. | |
| 6,558,331 B1 | 5/2003 | Davidsen et al. | |
| 6,709,392 B1 | 3/2004 | Salgo et al. | |
| 6,776,763 B2 | 8/2004 | Nix et al. | |
| 6,854,338 B2 | 2/2005 | Khuri-Yakub et al. | |
| 6,945,115 B1 * | 9/2005 | Wang | 73/718 |
| 6,958,255 B2 | 10/2005 | Khuri-Yakub et al. | |
| 6,999,000 B2 * | 2/2006 | Campbell et al. | 340/870.01 |
| 7,212,787 B2 * | 5/2007 | Wu et al. | 455/73 |
| 7,213,468 B2 | 5/2007 | Fujimoto | |
| 7,305,883 B2 * | 12/2007 | Khuri-Yakub et al. | 73/579 |
| 7,408,283 B2 * | 8/2008 | Smith et al. | 310/309 |

(Continued)

OTHER PUBLICATIONS

Translated Chinese Office Action mailed Jan. 18, 2012 for Chinese patent application No. 200880117482.1, a counterpart foreign application of U.S. Appl. No. 60/992,020, 14 pages.

Translated Chinese Office Action mailed Nov. 30, 2011 for Chinese patent application No. 200880117507.8, a counterpart foreign application of U.S. Appl. No. 12/745,758, 18 pages.

(Continued)

*Primary Examiner* — Ian J Lobo
(74) *Attorney, Agent, or Firm* — Lee & Hayes, PLLC

(57) ABSTRACT

Implementations of a cMUT have a telemetric antenna operative to telemetrically transmit an output signal generated by the cMUT in reception mode (RX). The cMUT generates the output signal by converting a received energy applied on the cMUT. The received energy may be an acoustic wave or a low-frequency pressure signal. The acoustic wave may be generated by a separate acoustic energy source. The cMUT may form a modulated signal using a carrier signal modulated with the output signal, and telemetrically transmit the modulated signal carrying the output signal to increase efficiency. The antenna may also receive an input signal from outside to telemetrically power on the cMUT.

19 Claims, 3 Drawing Sheets

(56) References Cited

U.S. PATENT DOCUMENTS

| | | |
|---|---|---|
| 7,880,565 B2 | 2/2011 | Huang |
| 8,018,301 B2 | 9/2011 | Huang |
| 2003/0236443 A1 | 12/2003 | Cespedes et al. |
| 2004/0085858 A1 | 5/2004 | Khuri-Yakub et al. |
| 2004/0229830 A1 | 11/2004 | Tachibana et al. |
| 2005/0004466 A1 | 1/2005 | Hynynen et al. |
| 2005/0015009 A1 | 1/2005 | Mourad et al. |
| 2005/0137812 A1 | 6/2005 | Schaffer et al. |
| 2005/0177045 A1 | 8/2005 | Degertekin et al. |
| 2005/0288873 A1 | 12/2005 | Urdaneta et al. |
| 2006/0004289 A1 | 1/2006 | Tian et al. |
| 2006/0084875 A1 | 4/2006 | Knight |
| 2006/0229659 A1 | 10/2006 | Gifford et al. |
| 2007/0013269 A1 | 1/2007 | Huang |
| 2007/0066902 A1 | 3/2007 | Wilser et al. |
| 2007/0093702 A1* | 4/2007 | Yu et al. .................. 600/326 |
| 2010/0013574 A1 | 1/2010 | Huang |
| 2010/0160786 A1* | 6/2010 | Nordgren et al. ............. 600/459 |
| 2011/0136284 A1 | 6/2011 | Huang |

OTHER PUBLICATIONS

Office action for U.S. Appl. No. 12/745,754, mailed on Jan. 9, 2012, Huang, "CMUT Packaging for Ultrasound System", 10 pages.

Non-Final Office Action for U.S. Appl. No. 12/745,749, mailed on Mar. 23, 2012, Yongli Huang, "CMUT Packaging for Ultrasound System", 12 pages.

Savoia et al., "Multilayer cMUT Structure for Improved Sensitivity and Bandwidth", 2006 IEEE Ultrasonics Symposium, pp. 1939-pp. 1942.

Translated Chinese Office Action mailed Jul. 25, 2012 for Chinese patent application No. 200880117507.8, a counterpart foreign application of U.S. Appl. No. 12/745,758, 7 pages.

Translated Chinese Office Action mailed Aug. 24, 2012 for Chinese patent application No. 200880117483.6, a counterpart foreign application of U.S. Appl. No. 12/745,758, 29 pages.

Office action for U.S. Appl. No. 12/745,754, mailed on Jul. 5, 2012, Huang, "CMUT Packaging for Ultrasound System", 10 pages.

\* cited by examiner

TELEMETRIC SENSING USING MICROMACHINED ULTRASONIC TRANSDUCER

RELATED APPLICATIONS

This application claims priority benefit of U.S. Provisional Patent Application No. 60/992,020 entitled "ENHANCED MICROMACHINED ULTRASONIC TRANSDUCERS", filed on Dec. 3, 2007, which application is hereby incorporated by reference in its entirety. This application is further related to International (PCT) Patent Application No. PCT/US07/65888, entitled "MODULATION IN MICROMACHINED ULTRASONIC TRANSDUCERS", filed on Apr. 3, 2007, which PCT application is hereby incorporated by reference in its entirety.

BACKGROUND

Capacitive micromachined ultrasonic transducers (cMUTs) are electrostatic actuators/transducers, which are widely used in various applications. Ultrasonic transducers can operate in a variety of media including liquids, solids and gas. Ultrasonic transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and numerous other practical applications. A typical structure of a cMUT is a parallel plate capacitor with a rigid bottom electrode and a movable top electrode residing on or within a flexible membrane, which is used to transmit/accurate (TX) or receive/detect (RX) an acoustic wave in an adjacent medium. A direct current (DC) bias voltage may be applied between the electrodes to deflect the membrane to an optimum position for cMUT operation, usually with the goal of maximizing sensitivity and bandwidth. During transmission an alternating current (AC) signal is applied to the transducer. The alternating electrostatic force between the top electrode and the bottom electrode actuates the membrane in order to deliver acoustic energy into the medium surrounding the cMUT. During reception an impinging acoustic wave causes the membrane to vibrate, thus altering the capacitance between the two electrodes.

Further improvements to the existing cMUT technology are needed to expand the scope of its applications.

SUMMARY

Implementations of a cMUT have a telemetric antenna operative to telemetrically transmit an output signal generated by the cMUT in reception mode (RX). The cMUT generates the output signal by converting a received energy applied on the cMUT. The received energy may be an acoustic wave or a low-frequency pressure signal. The acoustic wave may be generated by a separate acoustic energy source. The cMUT may form a modulated signal using a carrier signal modulated with the output signal, and telemetrically transmit the modulated signal carrying the output signal. The antenna may also receive an input signal from outside to power on the cMUT.

In one embodiment, the antenna has an inductive member such as an inductor. The inductive member may also serve to tune the impedance of the cMUT. Benefited by the high frequency of the carrier signal in the modulation technique, the inductive member for tuning may have very low inductance and therefore may be simple and small enough to be micromachined on a substrate. The inductive member and the cMUT can form a resonator with a frequency designed as the same as the frequency of the carrier signal. The resonator may also have an optional circuit to enhance the performance the resonator. In one embodiment, a switch circuit is included in the circuit so that the circuit is powered on only when triggered by the telemetric signal from outside.

Besides functioning as an ultrasound transducer, the disclosed telemetric cMUT may also telemetrically provide pressure and flow information by processing the demodulated output of the cMUT.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE FIGURES

The detailed description is described with reference to the accompanying figures. In the figures, the left-most digit(s) of a reference number identifies the figure in which the reference number first appears. The use of the same reference numbers in different figures indicates similar or identical items.

DETAILED DESCRIPTION

Disclosed is a technique to telemetrically (wireless) operate a CMUT. A carrier signal is modulated with the CMUT output signal by the cMUT into a modulated signal with a higher frequency so that the modulated signal can be detected by a telemetric signal efficiently.

The CMUT is a modulator of its capacitive signal (output signal) and the voltage (e.g. a carrier signal) applied on the cMUT. The cMUT's modulation function enables the cMUT to perform a telemetric operation as disclosed herein. A conventional PZT acoustic transducer does not have such properties.

The carrier signal may be generated by a signal source and applied on the CMUT through a cable. The carrier signal may also be generated by a signal source and telemetrically coupled into a circuit built with a CMUT. In one embodiment, the circuit built with the CMUT may include at least one inductive device (e.g., inductor or transformer) to form a resonator circuit with a resonator frequency designed to be the same as the carrier frequency. Optionally, the inductive device can be configured as an antenna for the telemetric operation. The carrier signal may be also generated by a resonator built with a CMUT.

The output signal of the CMUT can be extracted from the modulated signal received by a telemetric detection circuit. The telemetric circuit includes at least an antenna, and may also include an amplifier, a filter and a demodulator.

If the transmission signal is applied through a cable, the inductive device may also be used to tune the impedance of the CMUT so that it can receive the input signal from the cable more efficiently.

If the modulated signal is properly processed, the telemetric cMUT may not only be able to obtain an output from an impinged wave (e.g., an acoustic wave), but also be able to extract information of a static pressure and flow information in the medium.

Figure 1:
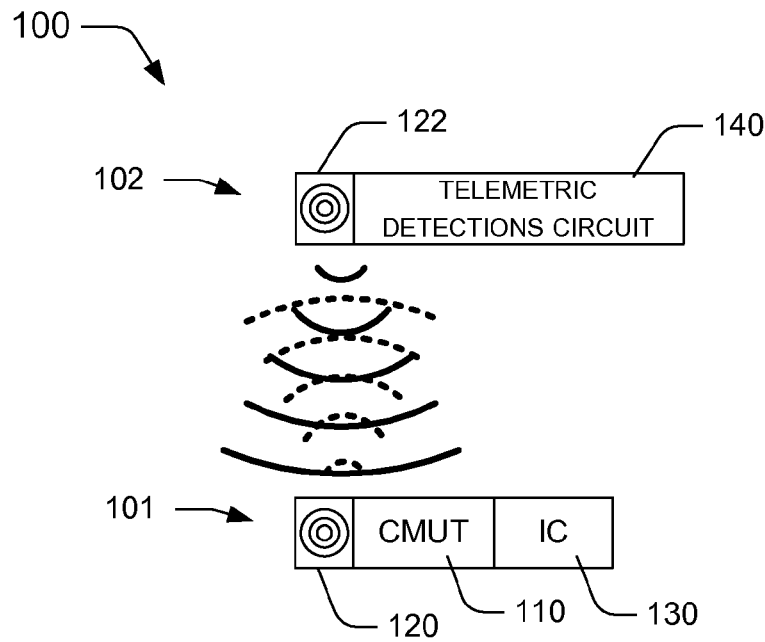
FIG. 1 illustrates a first exemplary embodiment of the telemetric cMUT.

FIG. 1 illustrates a first exemplary embodiment of the telemetric cMUT system. A telemetric cMUT system 100 has two subsystems: a cMUT unit 101 and a telemetric interface unit 102. The cMUT unit 101 is used for acoustic operation (detection and/or transmission) and pressure sensing, while the telemetric interface unit 102 is for receiving signals from the cMUT unit 101 or communicating to the cMUT unit 101.

The cMUT unit 101 has a cMUT 110, an antenna 120 and an integrated circuit (IC) 130. The details of the cMUT are not shown as they are not essential to the present disclosure. In principle, any cMUT, including both flexible membrane cMUTs and embedded spring cMUTs (EScMUTs), may be used. A suitable cMUT has a first electrode and a second electrode separated from each other by an electrode gap so that a capacitance exists between the electrodes. A spring member (e.g., a flexible membrane or a spring layer) supports one of the electrodes for enabling the two electrodes to move toward or away from each other. In a flexible membrane cMUTs, the spring member is a flexible membrane directly supporting one of the electrodes. In an EScMUT, the spring member is a spring layer supporting an electrode on a plate which is suspended from the spring layer by spring-plate connectors.

The cMUT 110 may be a single transducer that has at least one cMUT element, or a cMUT array of multiple cMUT elements. The cMUT 110 is operative in at least a reception mode (RX) to convert a received energy applied on the cMUT 110 to an output signal. The cMUT 110 may also be operative in the transmission of (TX) to convert an input signal to an actuation energy applied on a medium.

A telemetric antenna 120 is packaged with a cMUT 210. The antenna 120 is operative to telemetrically (wirelessly) transmit the output signal generated by the cMUT 110. In case where modulation is used, the antenna 120 is operative to telemetrically transmit a carrier signal modulated with the output signal. The term "antenna" is used in this description without any limitation. The antenna 120 may be any kind of a device that is adapted for telemetrically receive or transmit a radio-frequency (RF) signal. Any suitable antenna that is capable of wirelessly transducing (transmitting and/or receiving) electromagnetic waves may be used. The size and design of the antenna 120 may depend on the application. For micromachined ultrasonic transducers, the antenna 120 may be a simple antenna made of a small inductor such as an on-chip folded dipole antenna which can be fabricated together with the cMUT 110. The inductor may be made using a suitable semiconductor processing method, and may be fabricated monolithically with the cMUT 110.

An optional integrated circuit (IC) 130 is packaged with the cMUT 110. The IC 130 may include functional circuits such as a switch circuit to switch between the operations of cMUT, a control circuit and the power management circuit. For example, the IC 130 may include an oscillator to generator a high frequency carrier signal for signal modulation as described herein. Also, a switch circuit may be designed in a way to power on only when triggered by a telemetric signal from outside (e.g., a signal sent from the telemetric interface unit 102).

The telemetric interface unit 102 is placed nearby the cMUT unit 101 to telemetrically (wirelessly) receive the output signals transmitted from the cMUT unit 101. It may also be used to communicate to the cMUT unit 101 as described herein. The telemetric interface unit 102 has another telemetric antenna 122 connected to a telemetric detection circuit 140 to couple the signal between the cMUT 110 with the telemetric detection circuit 140. The communication between the cMUT 110 and the telemetric detection circuit 140 can be a one-way transmission or a two-way transmission.

The telemetric cMUT system 102 may not only provide acoustic information (such as ultrasonic imaging, distance measurement, and flow measurement), but in some embodiments may provide low-frequency pressure or flow information using a modulation technique in which a carrier signal is modulated with the cMUT output signal, as will be shown for the below.

Figure 2:
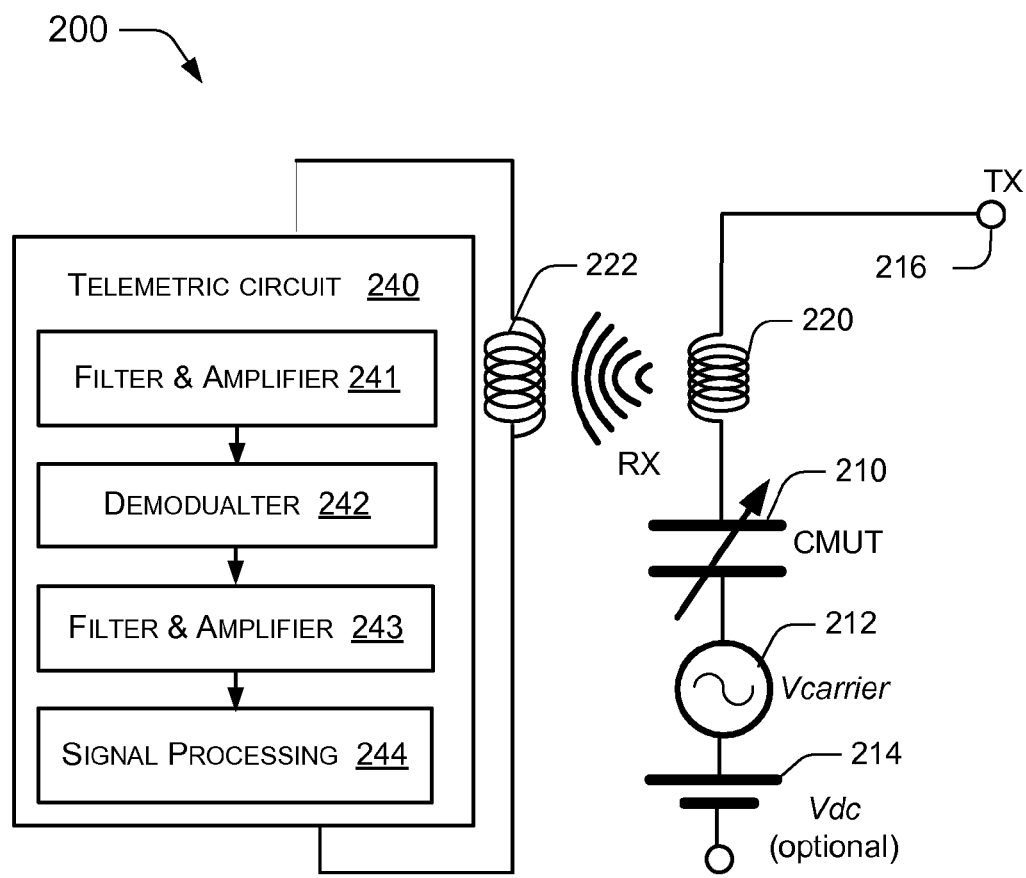
FIG. 2 illustrates a second exemplary embodiment of the telemetric cMUT system.

FIG. 2 illustrates a second exemplary embodiment of the telemetric cMUT system. The cMUT system 200 is similar to the cMUT system 100 of FIG. 1 but shows certain more components for detail. The cMUT system 200 is an implementation using a modulated signal to improve the cMUT reception.

Since the cMUT is a capacitive device, there is a cut-off in low frequency response of the cMUT if the cMUT is biased by DC voltage. The cMUT with a DC bias is an inefficient device at low frequency ranges, making conventional cMUT operation methods unsuitable for sensing low-frequency signals such as static pressure or flow variation. In order to solve this problem, a cMUT RX signal may be modulated with a higher frequency signal (carrier signal) to improve its sensitivity at low frequency range.

The cMUT system 200 has a cMUT 210, which is simplified as a variable capacitor. An AC signal 214 is applied to the cMUT 210 to provide a carrier signal Vcarrier. The AC signal may be generated by an AC signal source which is a part of the cMUT system 200, or connected externally. An optional DC bias signal Vdc is provided by a DC signal source 214 and is applied with the carrier signal Vcarrier to one side of the cMUT 210. In a reception mode, the cMUT 210 generates an output signal due to a variance of its capacitance caused by an actuation/excitation energy applied on the cMUT 210. The output signal and the AC carrier signal 212 (Vcarrier) generated by AC signal source are modulated by the cMUT to form a modulated signal. In one embodiment, the modulated signal may also include an optional DC bias (Vdc) generated by DC signal source 214.

For telemetric detection, the modulated signal carrying the output signal is transmitted by the antenna 220, received by the antenna 222 and processed by the telemetric circuit 240, which includes several components. If needed, the received signal passes through an amplifier/filter assembly 241 therefore it is sent to a demodulator 242 to be demodulated. The demodulated signal then passes through another amplifier/filter assembly 243 if needed. The signal is finally sent to signal process unit 244 to be processed.

The carrier signal 212 has a frequency higher than the frequency of output signal or the operating frequency of the cMUT system 210. The higher frequency carrier signal enables detection of low-frequency signals such as pressure signals, and also enables a telemetric detection of the cMUT output signal. The cMUT system 200 may be used to detect a wide range of actuation/excitation energies or forces applied on the cMUT 210, including ultrasonic acoustic waves and low-frequency signals such as pressure signals or flow information having a frequency substantially lower than an ultrasound frequency range. When properly designed, the cMUT system 200 is able to detect quasi-static pressure signals in a range of $0\text{ Hz} \leq \text{frequency} \leq 20\text{ kHz}$.

Another electrode of the cMUT 210 is connected to a transmission (TX) port 216 through a telemetric component (e.g., antenna) 220. The telemetric component 220 may be simply made of an inductive device, e.g. an inductor or transformer. By proper termination of TX port, the telemetric component 220 may serve the functions of both a telemetric antenna/receiver and an impedance tuning device for TX input.

More examples of using modulation in cMUT are disclosed in the incorporated International (PCT) Patent Application No. PCT/US07/65888, entitled "MODULATION IN MICROMACHINED ULTRASONIC TRANSDUCERS".

Usually, a cMUT performs both transmission and reception operations in the ultrasound imaging. However if the acoustic wave can be generated by another acoustic source or by any other kind of energy sources (e.g. optical light, laser light, etc.), the telemetric cMUT may be used only for reception as shown below.

Figure 3:
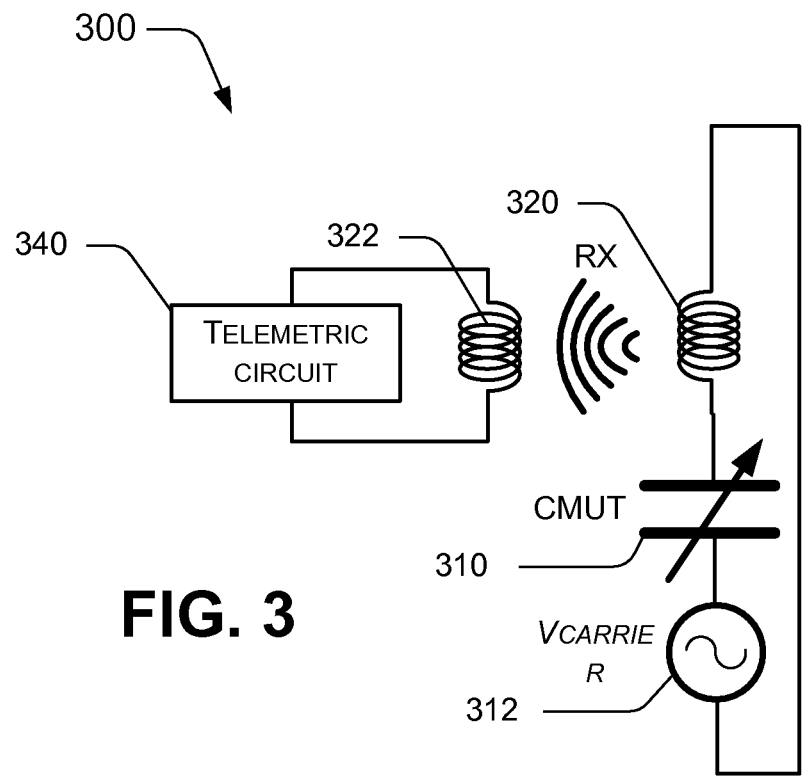
FIG. 3 illustrates a third exemplary embodiment of the telemetric cMUT system.

FIG. 3 illustrates a third exemplary embodiment of the telemetric cMUT system. The cMUT system 300 performs reception (RX) only. The cMUT system 300 has a cMUT 310. An AC carrier signal 312 is used for modulation similar to that described in FIG. 2. The carrier signal (Vcarrier) 312 is applied on one electrode of the cMUT 310. The carrier signal 312 may be introduced from outside or generated by an IC chip (not shown) which is integrated or assembled with the cMUT 310. A telemetric antenna 320 connects to an output port of the cMUT 310 to transmit the modulated signal (carrier signal carrying the output signal of the cMUT 310) telemetrically. Another antenna 322 telemetrically receives the modulated signal from the antenna 320. The antenna 322 connects to a telemetric circuit 340 which processes the received modulated signal in a similar manner described in FIG. 2.

Figure 4:
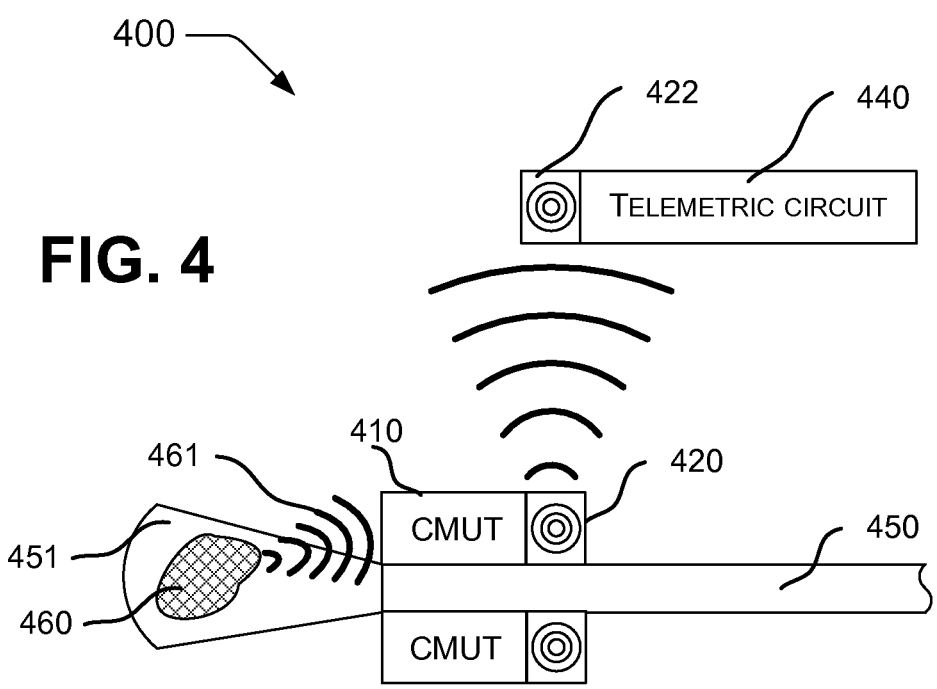
FIG. 4 illustrates a fourth exemplary embodiment of the telemetric cMUT system.

FIG. 4 illustrates a fourth exemplary embodiment of the telemetric cMUT system. The cMUT system 400 functions as an ultrasound receiver to detect ultrasound waves for ultrasound imaging. The cMUT system 400 uses a cMUT 410 connected to an antenna 420. An optical source 450 (e.g., an optical fiber) is used to generate acoustic energy 451 in a field occupied by an ultrasound imaging object 460. The acoustic energy 451 is scattered off the ultrasound imaging object 460 to generate acoustic waves 461. The acoustic waves 461 are sensed by the cMUT 410, which converts the acoustic energy to an output signal. The output signal is transmitted to outside by the antenna 420 and received by the antenna 422 and processed by telemetric circuit 440. The output signal may be carried in a modulated signal as described herein.

In FIG. 4, the CMUT 410 may be attached to one side of the optical source 450, or be packaged around the optical source 450. For example, the cMUT 410 may be in a cylinder shape having a central opening so that the optical source 450 can be placed into the opening when packaging the cMUT system 400.

Rather than only transform a signal from the cMUT to a telemetric circuit as described in some previous examples, the telemetric cMUT may also receive signals from outside for communication or energy transfer, as shown below.

Figure 5:
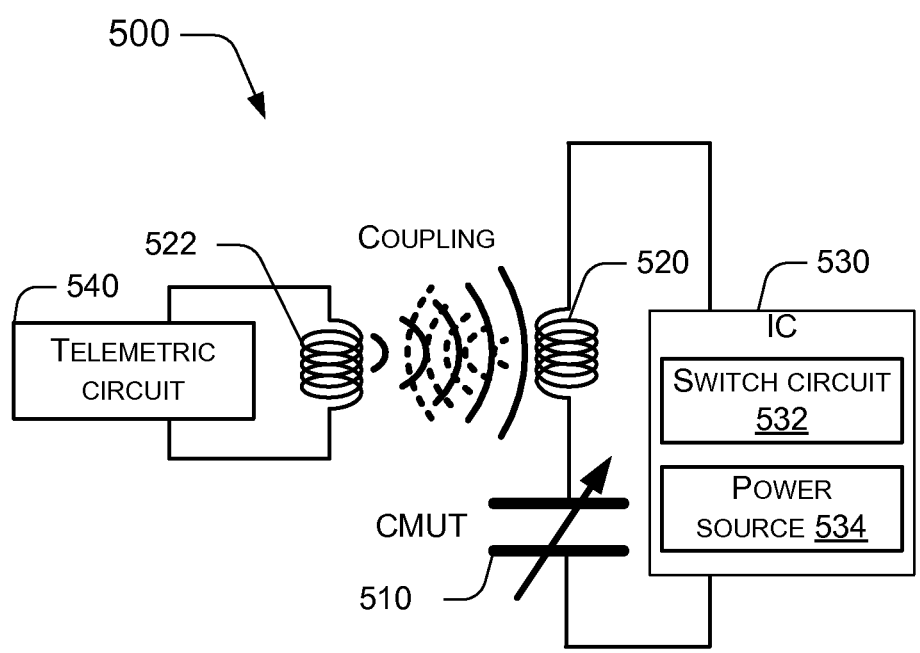
FIG. 5 illustrates a fifth exemplary embodiment of the telemetric cMUT system.

FIG. 5 illustrates a fifth exemplary embodiment of the telemetric cMUT system. The cMUT system 500 may either function as an ultrasound receiver to detect ultrasound waves for ultrasound imaging, or as a pressure or flow information sensor. The cMUT system 500 uses a cMUT 510 connected to an antenna 520 which is used for both transmitting an output signal of the cMUT 510 and receiving an input signal from the outside. An outside telemetric circuit 540 and an antenna 522 are used for both receiving the telemetrically transmitted output signal of the cMUT 510 and for transmitting an input signal to the cMUT 510. The input signal may either be a communication signal or as an energy source, or both. Antennas 520 and 522 form a telemetric coupling in this embodiment. Modulation using a carrier signal carrying the output signal of the cMUT 510 may also be implemented in this embodiment as described herein.

The cMUT 510 may have an optional IC 530. In one embodiment, the IC 530 is integrated or packaged with the cMUT 510 to enhance the performance. The antenna 520 may be an inductive member, which can be micromachined and packaged with the cMUT 510. Furthermore, in this embodiment, the variable capacitor of the cMUT 510, the inductive component (e.g., the antenna 520) and the optional IC 530 may form a resonator circuit with a resonant frequency preferably the same as the frequency of the modulation or the carrier signal.

The IC 530 may be powered by an internal power source 534 (e.g., battery, stored charges, etc.), but may optionally be powered telemetrically by an energetic coupling between the antennas 520 and 522. A switch circuit 532 may be included in the IC 530 so that the circuit of the IC 530 is powered on only when triggered by a telemetric signal from outside. The IC 530 may also provide a gain to the resonator formed mainly by the cMUT 510 and the inductive device 520.

The telemetric cMUT system may be advantageous used in a variety of applications and environments. One exemplary application of the disclosed telemetric cMUT system is a cMUT sensor adapted for placement inside a human body for sensing or imaging.

It is appreciated that the potential benefits and advantages discussed herein are not to be construed as a limitation or restriction to the scope of the appended claims.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A capacitive micromachined transducer (cMUT) system comprising:
   a cMUT operative in a reception mode (RX) to convert an external energy applied on the cMUT to an output signal;
   an AC signal source on a first side of the cMUT for generating a carrier signal that passes across an electrode gap of the cMUT to a second side of the cMUT, so that a carrier frequency of the carrier signal is modulated with the output signal, that is output by the cMUT, to become a modulated signal carrying the output signal; and
   an antenna on the second side of the cMUT to wirelessly transmit the modulated signal carrying the output signal.

2. The cMUT system of claim 1, wherein the external energy comprises an ultrasonic acoustic wave.

3. The cMUT system of claim 1, wherein the external energy comprises a pressure having a frequency substantially lower than an ultrasound frequency range.

4. The cMUT system of claim 3, wherein the frequency of the pressure is in a range of $0\ Hz \leq frequency \leq 20\ kHz$.

5. The cMUT system of claim 3, wherein the output signal modulates the carrier signal having the carrier frequency higher than the frequency of the pressure to create a modulated signal.

6. The cMUT system of claim 1, wherein the antenna comprises an inductive member.

7. The cMUT system of claim 6, wherein the inductive member is connected to the cMUT and has an inductance tuned for an impedance of the cMUT.

8. The cMUT system of claim 6, wherein the inductive member and the cMUT form a resonator having a resonant frequency at or around the carrier frequency.

9. The cMUT system of claim 1, the cMUT comprises a cMUT array having a plurality of cMUT elements.

10. The cMUT system of claim 9, wherein the plurality of cMUT elements each have an antenna comprising a respective inductive member.

11. The cMUT system of claim 1, the system further comprising a telemetric circuit including a switch circuit operative to power on the telemetric circuit when triggered by a telemetric signal received by the antenna from outside.

12. The cMUT system of claim 1, wherein the external energy comprises an acoustic wave generated by a separate source.

13. The cMUT system of claim 1, the system being adapted for placement inside a human body for sensing.

14. The cMUT system of claim 1, the system being operative in a transmission mode (TX) to convert an input signal to an actuation energy applied on a medium.

15. The cMUT system of claim 1, wherein the antenna is a first antenna, the cMUT system further comprising:
 a second antenna operative to receive the output signal wirelessly transmitted by the first antenna.

16. A capacitive micromachined transducer (cMUT) system comprising:
 a cMUT operative in at least a reception mode (RX) to convert a received energy applied on the cMUT to an output signal, the cMUT having a first electrode and a second electrode separated from each other by an electrode gap so that a capacitance exists between the first electrode and the second electrode, and a spring member supporting the second electrode for enabling the first electrode and the second electrode to move toward or away from each other;
 an AC signal source for generating a carrier signal on a first side of the cMUT so that the carrier signal passes across the electrode gap to a second side of the cMUT, wherein the cMUT is configured to modulate a carrier frequency of the carrier signal with the output signal to generate a modulated signal that includes the output signal; and
 an antenna on the second side of the cMUT to telemetrically transmit the modulated signal and/or to telemetrically receive an input signal.

17. The cMUT system of claim 16, wherein the cMUT is operative in the reception mode (RX) only, and the input signal is operative to telemetrically power on the cMUT.

18. A method for operating a capacitive micromachined transducer (cMUT) system, the method comprising:
 providing a cMUT operative in at least a reception mode (RX) to convert a received energy applied on the cMUT to an output signal;
 generating a carrier signal from a AC signal source on a first side of the cMUT, the carrier signal passing across an electrode gap of the cMUT to a second side of the cMUT, wherein a carrier frequency of the carrier signal is modulated, by the cMUT, with the output signal to produce a modulated signal having a modulated frequency; and
 transmitting the modulated signal carrying the output signal via an antenna on the second side of the cMUT.

19. The method as recited in claim 18, further comprising receiving, by a second antenna, the modulated signal transmitted by the first antenna.

* * * * *